(12) United States Patent
Dinsmore (10) Patent No.: US 6,480,568 B1
(45) Date of Patent: Nov. 12, 2002

(54) OPTICALLY DRIVEN THERAPEUTIC RADIATION SOURCE

(75) Inventor: Mark Dinsmore, Sudbury, MA (US)

(73) Assignee: Photoelectron Corporation, North Billerica, MA (US)

( * ) Notice: Subject to any disclaimer, the term of this patent is extended or adjusted under 35 U.S.C. 154(b) by 0 days.

(21) Appl. No.: 09/884,561

(22) Filed: Jun. 19, 2001

(51) Int. Cl.$^7$ ................................................ A61N 5/10
(52) U.S. Cl. ........................................ 378/65; 378/136
(58) Field of Search ............................ 378/64, 65, 119, 378/121, 136, 143

(56) References Cited

U.S. PATENT DOCUMENTS

| | | | |
|---|---|---|---|
| 5,090,043 A | 2/1992 | Parker et al. ................ | 378/121 |
| 5,153,900 A | 10/1992 | Nomikos et al. ............. | 378/65 |
| RE34,421 E | 10/1993 | Parker et al. ................ | 378/121 |
| 5,369,679 A | 11/1994 | Sliski et al. .................. | 378/65 |
| 5,422,926 A | 6/1995 | Smith et al. .................. | 378/65 |
| 5,428,658 A | 6/1995 | Oettinger et al. ........... | 378/119 |
| 5,621,780 A | 4/1997 | Smith et al. .................. | 378/65 |
| 6,148,061 A | * 11/2000 | Shefer et al. ............... | 378/121 |
| 6,319,188 B1 | 11/2001 | Lovoi ............................. | 600/3 |
| 6,320,935 B1 | 11/2001 | Shinar et al. ................ | 378/119 |
| 6,324,257 B1 | * 11/2001 | Halavee ...................... | 378/121 |

FOREIGN PATENT DOCUMENTS

| | | |
|---|---|---|
| WO | WO 93/04735 | 3/1993 |
| WO | WO 01/47596 | 5/2001 |

* cited by examiner

*Primary Examiner*—David P. Porta
*Assistant Examiner*—Therese Barber
(74) *Attorney, Agent, or Firm*—McDermott, Will & Emery (57) ABSTRACT

A miniaturized, optically driven therapeutic radiation source operates at significantly reduced power levels. The apparatus includes a laser-driven thermionic cathode, a target element, a probe assembly, and a laser source. The probe assembly includes an optical delivery structure, such as a fiber optic cable, that directs a laser beam from the laser source to impinge upon a surface of the thermionic cathode, heating the surface to a temperature sufficient to cause thermionic emission of electrons. The emitted electrons form an electron beam along a beam path. The target element is positioned in the beam path, and includes means for emitting therapeutic radiation, such as x-rays, in response to incident accelerated electrons from the electron beam. Reflector elements may be included to reflect unabsorbed laser radiation back to the thermionic cathode.

25 Claims, 7 Drawing Sheets

OPTICALLY DRIVEN THERAPEUTIC RADIATION SOURCE

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to therapeutic radiation sources, and more particularly to a reduced power, increased efficiency miniaturized radiation source that utilizes an optically driven thermionic cathode.

BACKGROUND OF THE INVENTION

In the field of medicine, therapeutic radiation such as x-ray radiation and γ-ray radiation is used for diagnostic, therapeutic and palliative treatment of patients. The conventional medical radiation sources used for these treatments include large, fixed position machines as well as small, transportable radiation generating probes. The current state-of-the-art treatment systems utilize computers to generate complex treatment plans.

Conventional radiation systems used for medical treatment utilize a high power remote radiation source, and direct a beam of radiation at a target area, such as a tumor inside the body of a patient. This type of treatment is referred to as teletherapy because the radiation source is located a pre-defined distance from the target. This treatment suffers from the disadvantage that tissue disposed between the radiation source and the target is exposed to radiation. Teletherapy radiation sources, which apply radiation to target regions internal to a patient from a source external to the target regions, often cause significant damage not only to the target region or tissue, but also to all surrounding tissue between the entry site, the target region, and the exit site.

Brachytherapy, on the other hand, is a form of treatment in which the source of radiation is located close to or in some cases within the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of a radioactive "seed," i.e. encapsulated radioactive isotopes which can be placed directly within or adjacent the target tissue to be treated. Handling and disposal of such radioisotopes, however, may impose considerable hazards to both the handling personnel and the environment.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body, is disclosed in U.S. Pat. No. 5,153,900 issued to Nomikos et al., U.S. Pat. No. 5,369,679 to Sliski et al., and U.S. Pat. No. 5,422,926 to Smith et al., all owned by the assignee of the present application, all of which are hereby incorporated by reference. The x-ray brachytherapy system disclosed in the above-referenced patents includes a miniaturized, insertable probe which is capable of generating x-ray radiation local to the target tissue, so that radiation need not pass through the patient's skin, bone, or other tissue prior to reaching the target tissue. The insertable probe emits low power x-rays from a nominal "point" source located within or adjacent to the desired region to be affected. In x-ray brachytherapy, therefore, x-rays can be applied to treat a predefined tissue volume without significantly affecting the tissue adjacent to the treated volume. Also, x-rays may be produced in pre-defined dose geometries disposed about a predetermined location. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy typically involves positioning the insertable probe into or adjacent to the tumor, or into the site where the tumor or a portion of the tumor was removed, to treat the tissue adjacent the site with a local boost of radiation. X-ray probes of the type generally disclosed in U.S. Pat. No. 5,153,900 include a housing, and a hollow, tubular probe or catheter extending from the housing along an axis and having an x-ray emitting target at its distal end. The probe may enclose an electron source, such as a thermionic cathode. In another form of an x-ray brachytherapy device, as disclosed in U.S. Pat. No. 5,428,658, an x-ray probe may include a flexible probe, such as a flexible fiber optic cable enclosed within a metallic sheath. The x-ray probe may also include a substantially rigid capsule that is coupled to a distal end of the flexible probe. The capsule encloses an electron source and an x-ray emissive target element. The electron source may be a photocathode. In a photocathode configuration, a photoemissive substance is irradiated by a LED or a laser source, causing the generation of free electrons. Typically, the flexible fiber optic cable couples light from a laser source or a LED to the photocathode.

In the devices disclosed in U.S. Pat. Nos. 5,133,900 and 5,428,658, an accelerating electric field may be established between the electron source and the target element. The established electric field acts to accelerate the electrons emitted from the electron source toward the target element. The target element emits radiation in response to incident electrons from the electron source.

In one form of a conventional thermionic cathode, a filament is heated resistively with a current. This in turn heats the cathode so that electrons are generated by thermionic emission. In one form of a conventional x-ray machine that uses such resistively heated thermionic cathodes, the cathode assembly may consist of a thoriated tungsten coil approximately 2 mm in diameter and 1 to 2 cm in length. When resistively heated with a current of 4 A or higher, the thoriated tungsten coil thermionically emits electrons. In one configuration, this coil is surrounded by a metal focusing cup which concentrates the beam of electrons to a small spot on an opposing anode which also functions as the target. The beam is focused on the anode to a spot diameter, usually ranging anywhere from about 0.3 to 2.5 millimeters. In many applications, most of the energy from the electron beam is converted into heat at the anode. To accommodate such heating, high power medical x-ray sources often utilize liquid cooling and a rapidly rotating anode. An increased effective target area is thereby established, permitting a small focal spot while minimizing the effects of localized heating.

To achieve good thermal conductivity and effective heat dissipation, the anode typically is fabricated from copper. In addition, the area of the anode onto which an electron beam is incident must be made from a material of high atomic number, in order for x-rays to be generated efficiently. To meet the requirements of thermal conductivity, effective heat dissipation, and efficient x-ray generation, a tungsten alloy is typically embedded in the copper.

It is desirable that the electron source be heated as efficiently as possible, namely that the thermionic cathode reach as high a temperature as possible using as little power as possible. In conventional x-ray tubes, for example, thermal vaporization of the tube's coiled cathode filament is frequently responsible for tube failure. Also, the anode heated to a high temperature can cause degradation of the radiation output. During relatively long exposures from an x-ray source, e.g. during exposures lasting from about 1 to about 3 seconds, the anode temperature may rise sufficiently to cause it to glow brightly, accompanied by localized surface melting and pitting which degrades the radiation output.

While a photocathode avoids such problems, one disadvantage of using a photocathode is the difficulty in fabricating the photocathode. A photocathode must have a sufficient quantum efficiency, where quantum efficiency relates to the number of electrons generated per incident light quantum. The degree of efficiency must be balanced to the intensity of available incident light. For practical substances, with reasonable quantum efficiencies above $10^{-3}$, the fabrication of the photocathode should be performed in a vacuum. As disclosed in U.S. Pat. No. 5,428,658, owned by the assignee of the present application and hereby incorporated by reference, in one form the vacuum fabrication can be carried out with the fiber optic cable positioned in a bell jar. By way of example, an Ag—O—Cs photosurface can be fabricated in the conventional manner. Subsequently, without exposure to air, the fiber optic cable can be inserted into the tubular probe, and the end of the fiber optic cable can be vacuum sealed to the probe.

It is an object of this invention to provide an increased efficiency, miniaturized radiation source having significantly reduced power requirements. It is another object of this invention to provide a miniaturized radiation source in which the electron source can generate electrons with minimal heat loss, without requiring a vacuum-fabricated photocathode. It is yet another object of this invention to provide a miniaturized radiation source in which laser energy is used to heat a thermionic cathode, instead of heating a thermionic cathode via conventional ohmic heating. In this way, electrons can be produced in a quantity sufficient to form an electron current necessary for generating therapeutic radiation at the target, while significantly reducing the requisite power requirements for the radiation source.

In order to reduce the power requirements for the laser-heated therapeutic radiation source discussed above, it is necessary to minimize heat loss by the thermionic cathode. Heat loss in a laser-heated thermionic cathode includes 1) heat lost by thermal conduction; 2) heat loss caused by the portion of the incident laser radiation that remains unabsorbed; and 3) heat loss by thermal radiation. It is yet another object of this invention to increase the efficiency of a laser-heated thermionic cathode in a radiation source, by reducing the amount of heat that is lost due to incident laser radiation that remains unabsorbed by the thermionic cathode.

SUMMARY OF THE INVENTION

The present invention is directed to a miniaturized source of therapeutic radiation having a low power, electron-beam activated radiation source. In particular, the apparatus of the present invention includes a thermionic cathode heated by a source of optical radiation, preferably a laser. By using a laser to heat a thermionic cathode to an electron emitting temperature, the power requirements for the therapeutic radiation source are significantly reduced. Therapeutic radiation generated by the apparatus of the present invention may include, but is not limited to, x-rays. In medical applications, the apparatus may be fully or partially implanted into, or surface mounted onto a desired area of a host, so as to irradiate a pre-selected region with therapeutic radiation. The apparatus of the present invention can operate at a relatively low voltage, for example in the range of approximately 10 keV to 90 keV, with electron currents for example in the range of from approximately 1 nA to about 1 mA.

A therapeutic radiation source in accord with the present invention includes a radiation generator assembly, a source of optical radiation, and a probe assembly. The source of optical radiation is preferably a laser that generates a substantially monochromatic, coherent beam of radiation. The radiation generator assembly includes an electron source for emitting electrons to generate an electron beam along a beam path, and a target element positioned in the beam path. The electron source is preferably a thermionic cathode having an electron emissive surface. The target element includes means for emitting therapeutic radiation in response to incident accelerated electrons from said electron beam. In a preferred embodiment, the target element is spaced apart from and opposite the electron emissive surface of the thermionic cathode. The target element includes at least one radiation emissive element adapted to emit therapeutic radiation in response to incident accelerated electrons from the thermionic cathode. The therapeutic radiation source also includes means for providing an accelerating voltage so as to establish an accelerating electric field which acts to accelerate electrons emitted from said electron source toward the target element.

In one embodiment, the radiation generator assembly further includes a substantially rigid capsule which encloses the electron source and the target element. Preferably, the electron source is at its proximal end, and the target element is at its distal end. The capsule is evacuated and preferably includes a radiation transmissive region.

The probe assembly includes an optical delivery structure, preferably a fiber optic cable, having a proximal end and a distal end. The distal end of the fiber optic cable is coupled to the radiation generator assembly. The fiber optic cable transmits optical radiation, generated by the source and incident on the proximal end, to the distal end. The fiber optic cable directs a beam of the transmitted optical radiation to impinge upon a surface of the thermionic cathode, wherein the beam of optical radiation has a power level sufficient to heat at least a portion of a surface of the thermionic cathode to an electron emitting temperature so as to cause thermionic emission of electrons from the surface. In one embodiment, the probe assembly includes a flexible metallic sheath enclosing the fiber optic cable.

In one embodiment, the means for providing the accelerating voltage is a power supply having a first terminal and a second terminal, and having drive means for establishing an output voltage between the first terminal and the second terminal. In one form, the power supply may be electrically coupled to the target element by way of the first and second terminals. The first terminal of the power supply can be electrically coupled to the electron emissive surface of the thermionic cathode, and the second terminal electrically coupled to the target element, thereby establishing an electric field which accelerates electrons emitted from the thermionic cathode toward the target element.

In a preferred embodiment, the apparatus of the present invention includes one or more reflector elements disposed at predetermined locations along an inner surface of the housing. The reflector elements are operative to reflect incident laser radiation unabsorbed by the thermionic cathode back to the thermionic cathode, thereby increasing the efficiency of the therapeutic radiation source.

DETAILED DESCRIPTION

The present invention is directed to a miniaturized, low power therapeutic radiation source which can be used for diagnostic, therapeutic and palliative treatment of patients. Generally, the apparatus of the present invention includes an electron-beam activated therapeutic radiation source, which operates at voltages in the range of approximately 10 keV to 90 keV, and electron beam currents in the range of approximately 1 nA to about 1 mA. At those operating voltages and currents, radiation output is relatively low, and the apparatus may be made small enough to be adapted for implantation in medical therapeutic applications. In view of the low-level radiation output, adequate tissue penetration and cumulative dosage may be attained by positioning the radiation source adjacent to or within the region to be irradiated. Thus, therapeutic radiation is emitted from a well-defined, small source located within or adjacent to the region to be irradiated.

The present invention seeks to significantly reduce the power requirements for such miniaturized therapeutic radiation sources, by heating a thermionic cathode with laser energy, instead of resistively heating the thermionic cathode with a current.

Figure 1A:
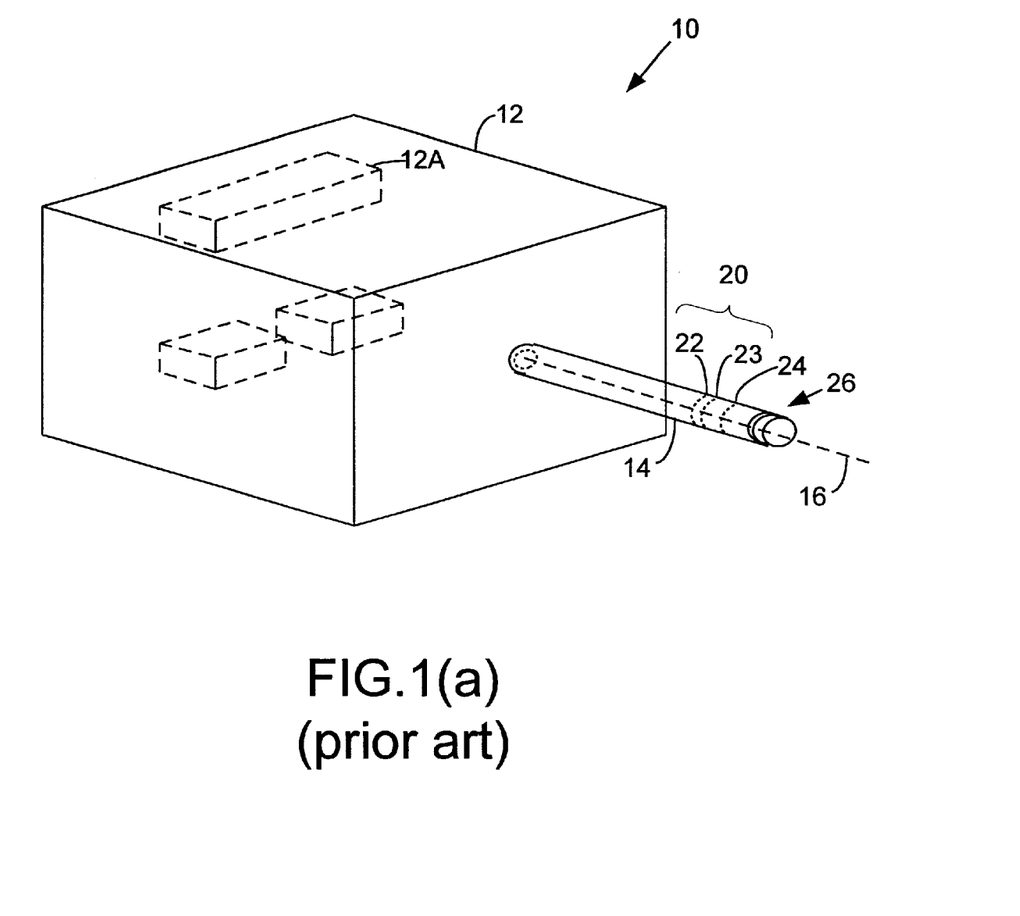
FIG. 1(a) is a diagrammatic perspective view of a therapeutic radiation source having a resistively heated thermionic cathode.

FIG. 1(a) shows a therapeutic radiation source 10 that generates and delivers therapeutic radiation in the form of x-rays. The miniaturized, low power x-ray source 10 shown in FIG. 1(a) is a prior art x-ray brachytherapy system having a thermionic cathode that is heated using conventional resistive heating. A suitable system is described in detail for example in the above-referenced U.S. Pat. No. 5,153,900, entitled "Miniaturized Low Power X-Ray Source." The system includes a housing 12 and an elongated, cylindrical probe 14 extending from the housing along a reference axis 16 and having a target assembly 26 at its distal end. The probe 14 may be flexible or rigid, and is integral with the housing 12. The housing 12 encloses a high voltage power supply 12A. The probe 14 is a hollow tube, and encloses an electron source 20. The electron source 20 includes a thermionic cathode 22 that may be driven by a floating low voltage power supply. In one embodiment, the electron source 20 may also include an annular focusing electrode 23, in which case the thermionic cathode 22 is located in proximity to the annular focusing electrode 23, which is typically at nearly the same potential as the cathode. The probe 14 extends along the same axis as the cathode 22 and the focusing electrode 23.

The probe 14 may be a hollow evacuated cylinder made of a beryllium (Be) cap and molybdenum-rhenium (Mo—Re), molybdenum (Mo) or mu-metal body. The length of the probe 14 may be determined in view of the body region to be treated. For example, the cylinder may be 15 cm in length, with an interior diameter of 4 mm, and an exterior diameter of 5 mm. Different geometries of the probe 14 may be used for different body regions. The main body of the probe 14 can be made of a magnetically shielding material such as a mu-metal. Alternatively, the probe 14 can be made of a non-magnetic metal, preferably having relatively high values for Young's modulus and elastic limit. Examples of such material include molybdenum, rhenium, or alloys of these materials. The inner or outer surface of probe can then be coated with a high permeability magnetic alloy such as permalloy (approximately 80% nickel and 20% iron), to provide magnetic shielding. Alternatively, a thin sleeve of mu-metal can be fitted over, or inside of, the probe 14. The prior art x-ray apparatus 10 can then be used in environments in which there are dc and ac magnetic fields due to electrical power, the field of the earth, or other magnetized bodies nominally capable of deflecting the electron beam from the probe axis.

Figure 1B:
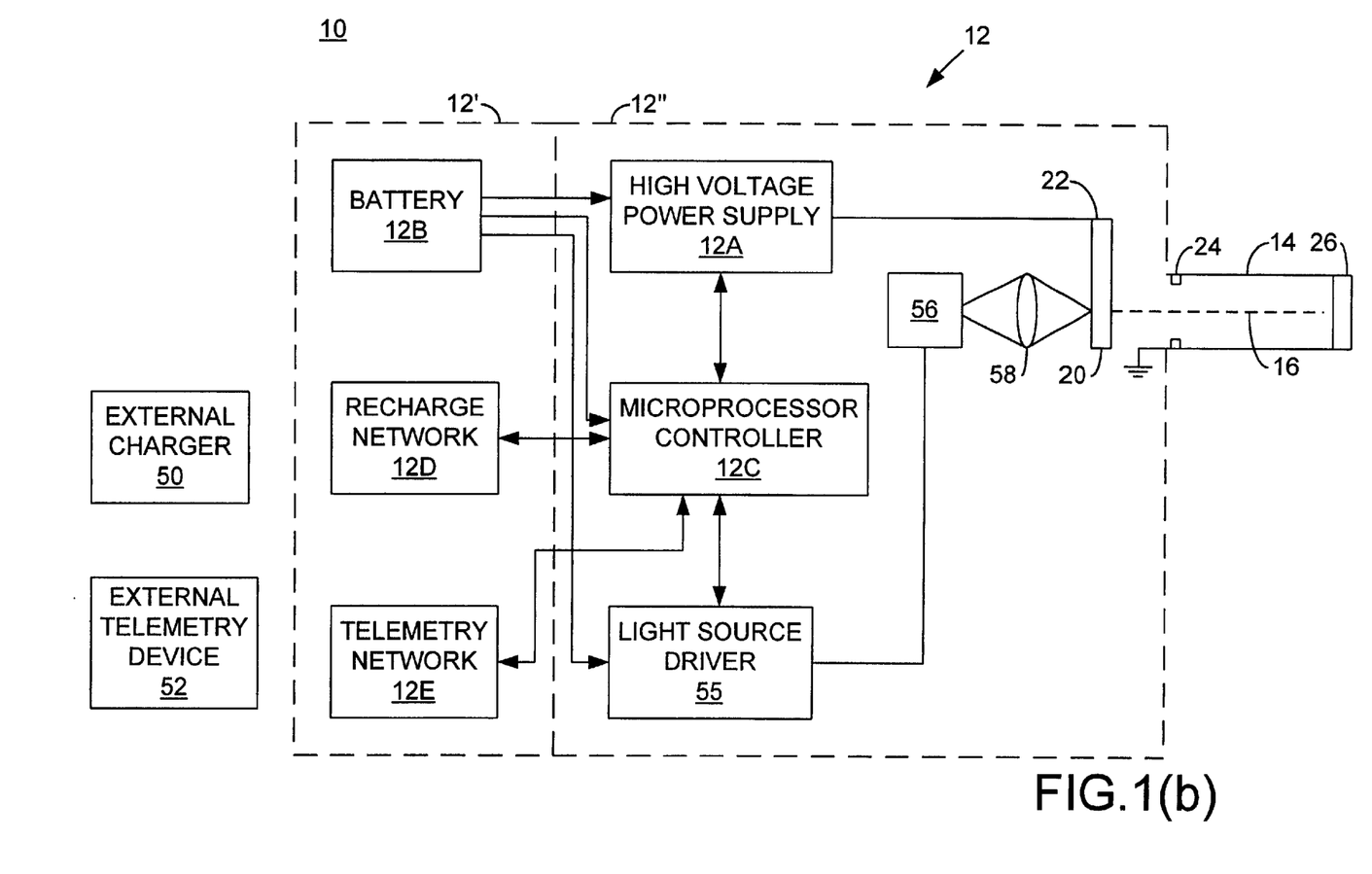
FIG. 1(b) is a schematic representation of a therapeutic radiation source having a resistively heated thermionic cathode.

FIG. 1(b) is a schematic representation of the prior art x-ray source apparatus 10 shown in FIG. 1(a). In this schematic representation, the housing 12 is represented as being divided into a first portion 12' and a second portion 12". Enclosed within the first housing portion 12' is a rechargeable battery 12B, a recharge network 12D for the battery, which is adapted for use with an external charger 50, and a telemetry network 12E, adapted to be responsive to an external telemetry device 52 to function. The first housing portion 12' is coupled by suitable communication means to the second housing portion 12". The second housing portion 12" includes a high voltage power supply 12A, the controller 12C, and the probe 14, as well as an electron beam generator. In the illustrated prior art apparatus, the electron beam generator includes a photocathode 22 driven by an associated light source driver 55 and diode laser 56 and associated lens assembly 58. In operation, the laser 56 illuminates the photocathode 22, which in turn generates electrons which are then accelerated toward the anode 24. The anode 24 attracts the electrons, then passes them through its central aperture toward the target assembly 26. The microprocessor 12C controls the power supply 12A and the light source driver 55 to dynamically adjust the cathode voltage, the electron beam current, and temporal parameters, or to provide pre-selected voltage, beam current, and temporal parameters.

As illustrated in FIG. 1(b), the external telemetry device 52 and telemetry network 12E may cooperate to permit external control, either dynamic or predetermined, over the power supply 12A and temporal parameters. Alternatively, the housing 12" may not be implanted into a host, and only the probe 14 may extend into a patient's body. In this case, the controller 12C may be used directly to control the operation of the apparatus, and there is no need for the network 12E.

In the above-described prior art x-ray source 10, the x-ray emissive element of the target 26 is adapted to be adjacent to or within the region to be irradiated. The proximity of the emissive element to the targeted region, e.g. the tumor, eliminates the need for the high voltages of prior art machines, in order to achieve satisfactory x-ray penetration through the body wall to the tumor site. The low voltage also concentrates the radiation in the targeted tumor, and limits the damage to surrounding tissue and surface skin at the point of penetration.

Figure 2:
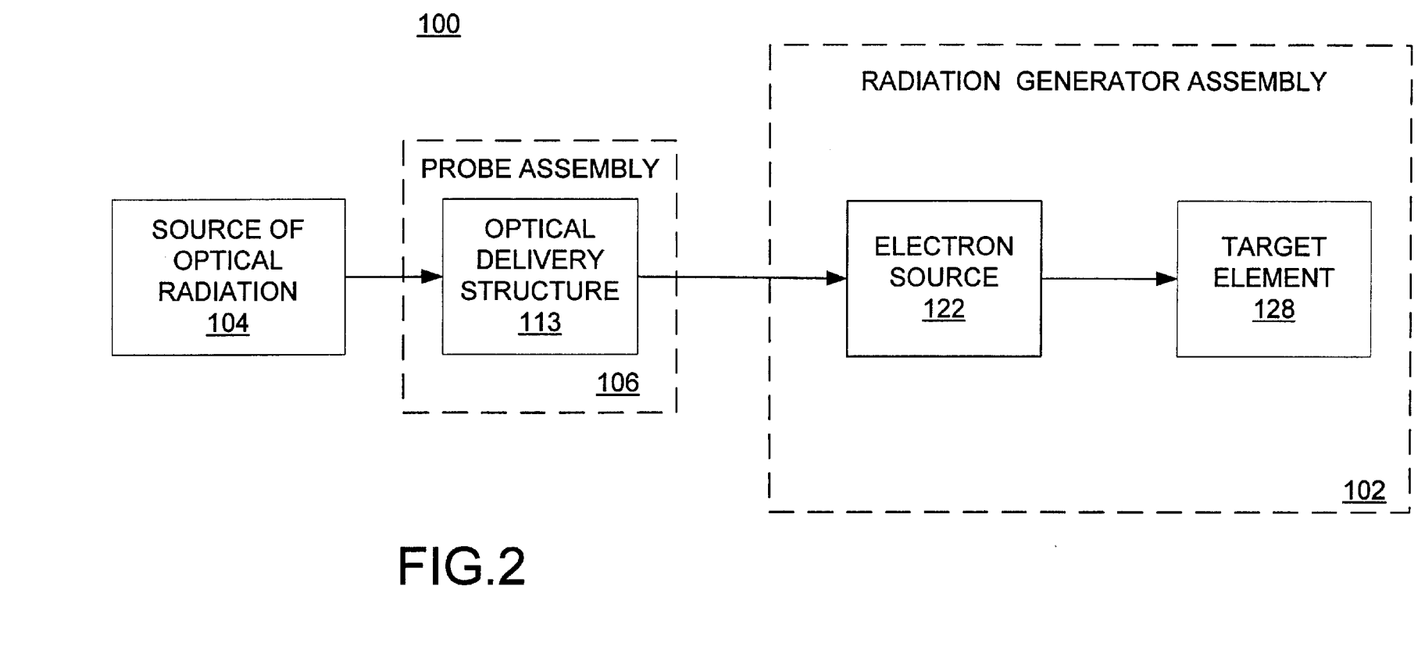
FIG. 2 is a schematic block diagram of an overview of a therapeutic radiation source constructed according to the present invention, and having a laser-heated thermionic cathode.

FIG. 2 is a schematic block diagram of an overview of one embodiment of a therapeutic radiation source 100, constructed according to the present invention. The therapeutic radiation source 100 includes a laser-heated thermionic cathode, in contrast to the prior art therapeutic radiation sources (shown in FIGS. 1(a) and 1(b)), which included a resistively heated thermionic cathode, or a photocathode. Heating the thermionic cathode 122 with a laser, instead of a current, significantly reduces the power requirements for a therapeutic radiation source 100 constructed in accordance with the present invention. In overview, the therapeutic radiation source 100 includes a radiation generator assembly 101, a source 104 of optical radiation, and a probe assembly 106. Preferably, the source 104 of optical radiation is a laser, so that the optical radiation generated by the source 104 is substantially monochromatic, and coherent. The laser may be a diode laser, by way of example; however other lasers known in the art may be used, such as a Nd:YAG laser, a Nd:YVO$_4$ laser, or a molecular laser. Alternatively, other sources of high intensity light may be used, such as LEDs (light emitting diodes). The radiation generator assembly 101 includes an electron source 122, and a target element 128 that includes means for emitting therapeutic radiation in response to incident accelerated electrons. Preferably, the electron source 122 is a thermionic cathode 122. The probe assembly 106 includes an optical delivery structure 113, such as a fiber optic cable. The optical delivery structure 113 directs a beam of laser radiation generated by the laser source 104 onto the thermionic cathode 122. The laser beam heats the thermionic cathode 122 so as to cause thermionic emission of electrons.

Figure 3:
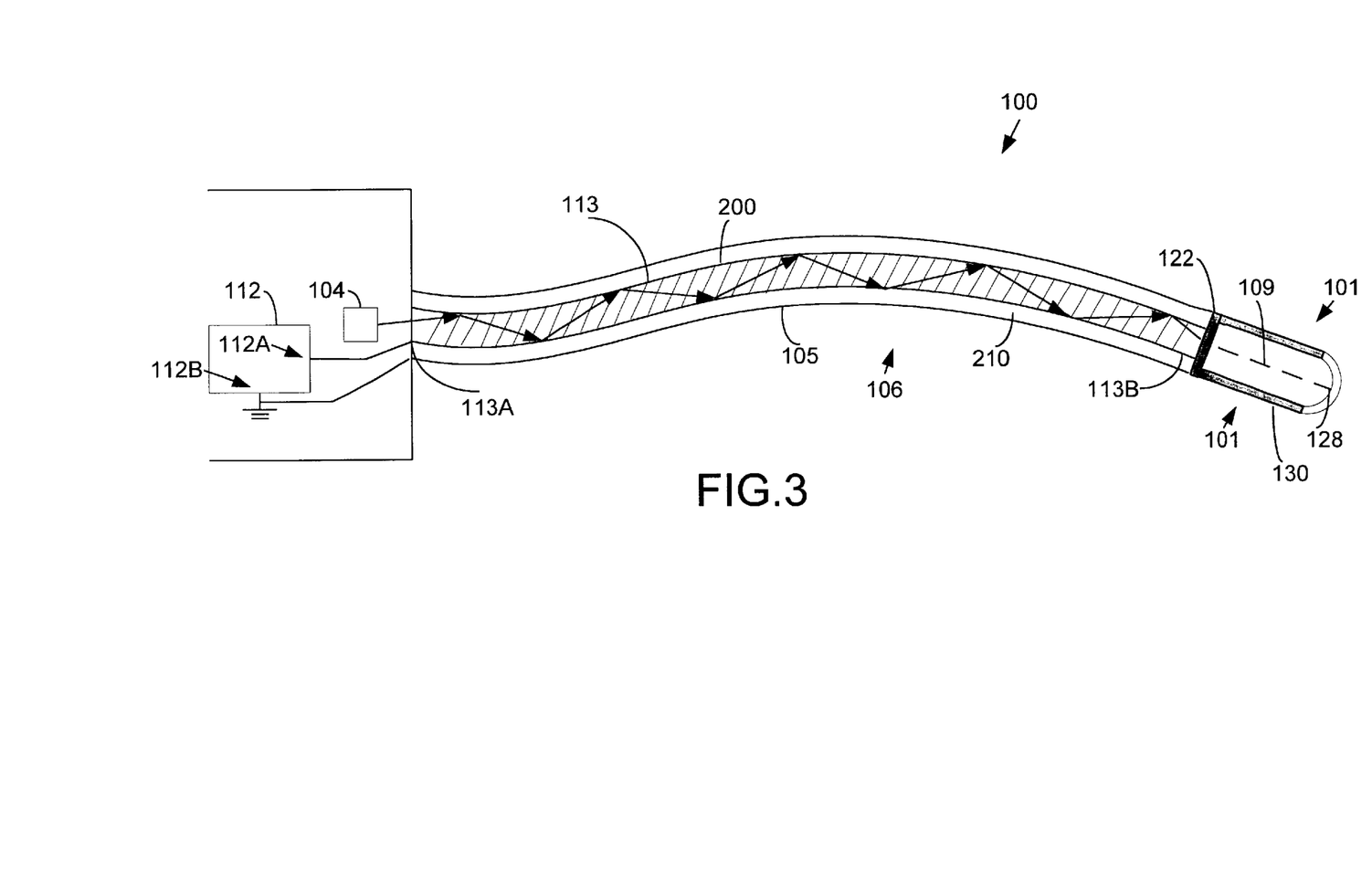
FIG. 3 is a diagrammatic view of one embodiment of a source of therapeutic radiation constructed according to the present invention, illustrating a laser source, a probe assembly and a radiation generator assembly embodying the present invention.
Figure 4:
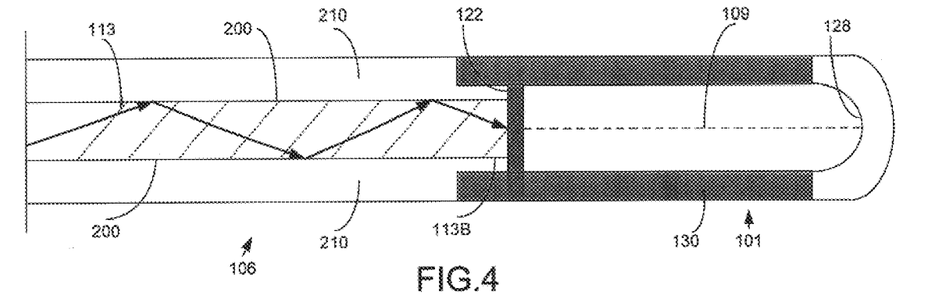
FIG. 4 is an enlarged diagrammatic view of one embodiment of a probe assembly and a radiation generator assembly, constructed according to the present invention.

FIGS. 3 and 4 illustrate a diagrammatic view of one embodiment of the therapeutic radiation source 100 constructed according to the present invention. In the embodiment illustrated in FIG. 3, the therapeutic radiation source 100 includes a laser source 104, a probe assembly 106, and a radiation generator assembly 101. The radiation generator assembly 101 includes an electron source 122 that generates an electron beam along a beam path 109, and a target element 128 positioned in the beam path 109. The therapeutic radiation source 100 also includes means for providing an accelerating voltage between the electron source 122 and the target element 128. In the illustrated embodiment, the means for providing the accelerating voltage is a high voltage power supply 112. The probe assembly 106 couples the laser source 104 and the high voltage power supply 112 to the radiation generator assembly 101. FIG. 3 provides an overall view of the therapeutic radiation source 100, whereas FIG. 4 provides an enlarged view of 1) the radiation generator assembly 101, and 2) the distal end of the probe assembly 106.

Referring to both FIGS. 3 and 4, the probe assembly 106 includes an optical delivery structure 113 having a proximal end 113A and a distal end 113B. The optical delivery structure 113 is enclosed within a flexible, electrically conductive catheter 105. The distal end 113B of the optical delivery structure 113 is affixed to the radiation generator assembly 101. In a preferred embodiment, the optical delivery structure 113 is a flexible fiber optic cable, extending from the proximal end 113A to the distal end 113B. In this embodiment, the flexible catheter 105 that encloses the fiber optic cable 113 is a small-diameter, flexible, metallic sheath.

In a preferred embodiment, the fiber optic cable 113 includes an electrically conductive outer surface 200. For example, the outer surface of the fiber optic cable 113 may be made conductive by applying an electrically conductive coating. The electrically conductive outer surface 200 of the fiber optic cable 113 provides a connection to the thermionic cathode 122 from the high voltage power supply 112. In this embodiment, the radiation generator assembly 101 also has an electrically conductive outer surface. Preferably, both the flexible metallic sheath 105 and the outer conductive surface of the radiation generator assembly 101 are set at ground potential, in order to reduce the shock hazard of the device. The flexible sheath 105 couples a ground return from the target element 128 to the high voltage power supply 112, thereby establishing a high voltage field between the thermionic cathode 122 and the target element 128. In an exemplary embodiment, the fiber optic cable 113 may have a diameter of about 200 microns, and the flexible metallic sheath 105 may have a diameter of about 1.4 mm. A layer 210 of dielectric material provides insulation between the outer surface of the fiber optic cable 113 and the inner surface of the metallic sheath 105.

As shown in FIGS. 3 and 4, the radiation generator assembly 101 includes the electron source 122, and the target element 128. The radiation generator assembly 101, which can be for example about 0.5 to about 2 cm in length, extends from the distal end of the probe assembly 106 and includes a shell or capsule 130 which encloses the electron source 122 and the target element 128. According to one embodiment, the capsule 130 is rigid in nature and generally cylindrical in shape. In this embodiment, the cylindrical capsule 130 enclosing the other elements of the radiation generator assembly 101 can be considered to provide a substantially rigid housing for the electron source 122 and the target element 128. In this embodiment, the electron source 122 and the target element 128 are disposed within the housing 130, with the electron source 122 disposed at a proximal end of the capsule 130, and the target element 128 disposed at a distal end of the capsule 130.

The capsule 130 defines a substantially evacuated interior region extending along the beam axis 109, between the electron source 122 at the proximal end of the capsule 130 and the target element 128 at the distal end of the capsule 130. The inner surface of the radiation generator assembly 101 is lined with an electrical insulator or semiconductor, while the external surface of the assembly 101 is electrically conductive, as mentioned earlier. A low secondary emission, controlled sheet resistance semiconducting film maximizes the high voltage breakdown voltage of the system. According to a preferred embodiment, the radiation generator assembly 101 is hermetically sealed to the end of the probe assembly, and evacuated. According to another embodiment, the entire probe assembly 106 is evacuated.

In the illustrated preferred embodiment of the invention, the electron source 122 is a thermionic cathode 122 having an electron emissive surface. In an alternative form of the invention (not shown), an annular focusing electrode may also be provided. In the alternative embodiment, the thermionic cathode 122 may be located in close proximity to the annular focusing electrode, which may be at nearly the same potential as the cathode.

In the embodiments illustrated in FIGS. 3 and 4, the means for establishing an accelerating electric field is the high voltage power supply 112. The power supply 112 has a first terminal 112A and a second terminal 112B, and has drive means for establishing an output voltage between the first terminal 112A and the second terminal 112B. In one form, the power supply 112 may be electrically coupled to the target element by way of the first and second terminals. The first terminal 112A of the power supply 112 is electrically coupled to the electron emissive surface of the thermionic cathode 122, and the second terminal 112B is electrically coupled to the target element 128.

In the illustrated embodiment, the high voltage power supply 112 provides a high potential difference across the conductive outer surface 200 of the fiber optic cable, and the metallic sheath 105, to establish an acceleration potential difference between the thermionic cathode 122 and the grounded target element 128. In this way, electrons emitted from the thermionic cathode 122 are accelerated toward the target element 128, and an electron beam is generated. The electron beam is preferably thin (e.g. 1 mm or less in diameter), and is established along a beam path 109 along a nominally straight reference axis that extends to the target element 128. The target element 128 is positioned in the beam path 109. The distance from the electron source 122 to the target element 128 is preferably less than 2 mm.

The high voltage power supply 112 preferably satisfies three criteria: 1) small in size; 2) high efficiency, so as to enable the use of battery power; and 3) independently variable x-ray tube voltage and current, so as to enable the unit to be programmed for specific applications. Preferably, the power supply 112 includes selectively operable control means, including means for selectively controlling the amplitude of the output voltage and the amplitude of the beam generator current. A high-frequency, switch-mode power converter is preferably used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components. A more detailed description of an exemplary power supply suitable for use as the power supply 112 is provided in U.S. Pat. Nos. 5,153,900 and 5,428,658.

The target element 128 is preferably spaced apart from and opposite the electron emissive surface of the thermionic cathode 122, and has at least one radiation emissive material adapted to emit therapeutic radiation in response to incident accelerated electrons from the electron emissive surface of the thermionic cathode 122. In a preferred embodiment, the emitted therapeutic radiation consist of x-rays, however it should be noted that the scope of this invention is not limited to x-rays, and other forms of therapeutic radiation may also be generated. In one embodiment, the target element 128 is a small beryllium (Be) substrate, coated on the side exposed to the incident electron beam with a thin film or layer of a high-Z, x-ray emissive element, such as tungsten (W), uranium (U) or gold (Au). By way of example, when the electrons are accelerated to 30 keV-, a 2 micron thick gold layer absorbs substantially all of the incident electrons, while transmitting approximately 95% of any 30 keV-, 88% of any 20 keV-, and 83% of any 10 keV-x-rays generated in that layer. In this embodiment, the beryllium substrate is 0.5 mm thick. With this configuration, 95% of the x-rays generated in directions normal to and toward the beryllium substrate, and having passed through the gold layer, are then transmitted through the beryllium substrate and outward at the distal end of the probe assembly 106.

In some forms of the invention, the target element 128 may include a multiple layer film, where the differing layers may have different emission characteristics. By way of example, the first layer may have an emission versus energy peak at a relatively low energy, and the second underlying layer may have an emission versus energy peak at a relatively high energy. With this form of the invention, a low energy electron beam may be used to generate x-rays in the first layer, to achieve a first radiation characteristic, and high energy electrons may be used to penetrate through to the underlying layer, to achieve a second radiation characteristic. As an example, a 0.5 mm wide electron beam may be emitted at the cathode and accelerated to 30 keV, with 0.1 eV transverse electron energies, and may arrive at the target element 128, with a beam diameter of less than 1 mm at the target element 128. X-rays are generated in the target element 128 in accordance with pre-selected beam voltage, current, and target element composition. The x-rays thus generated pass through the beryllium substrate with minimized loss in energy. As an alternative to beryllium, the target substrate may be made of carbon, ceramic such as boron nitride, or other suitable material which permits x-rays to pass with a minimum loss of energy. An optimal material for target substrate is carbon in its diamond form, since that material is an excellent heat conductor. Using these parameters, the resultant x-rays have sufficient energy to penetrate into soft tissues to a depth of a centimeter or more, the exact depth dependent upon the x-ray energy distribution.

In another embodiment of the invention, the target may be a solid, high-Z material, with x-rays being emitted in an annular beam perpendicular to the tube axis.

In the above embodiments, the probe assembly 106, along with its associated radiation generator assembly 101, can be coated with a biocompatible outer layer, such as titanium nitride on a sublayer of nickel. For additional biocompatibility, a sheath of, for example, polyurethane can be fitted over the probe.

Figure 5:
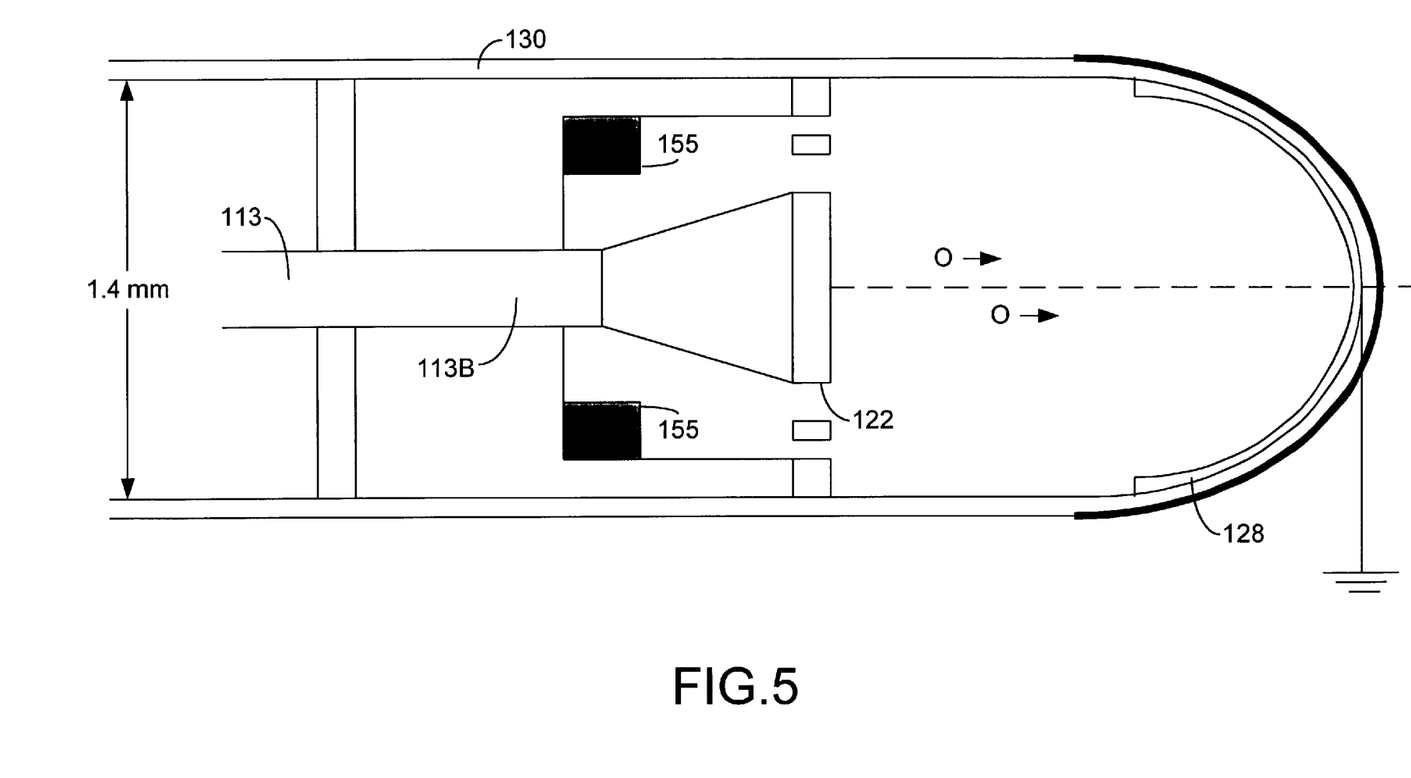
FIG. 5 is an enlarged view of one end of a radiation generator assembly embodying the present invention, illustrating an electron source having a laser-heated thermionic cathode.

FIG. 5 illustrates an electron source constructed according to the present invention, and including a laser-heated thermionic cathode 122. The cathode disc can be held in place by means of swage of the end or by laser welding. The thermionic cathode 122 has an electron emissive surface, and is typically formed of a metallic material. Suitable metallic materials forming the cathode 122 may include tungsten, thoriated tungsten, other tungsten alloys, thoriated rhenium, and tantalum. In one embodiment, the cathode 122 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 122 may also be an oxide coated cathode, where a coating of the mixed oxides of barium and strontrium, by way of example, may be applied to a metallic base, such as nickel or a nickel alloy. The metallic base may be made of other materials, including Group VI metals such as tungsten.

Getters 155 may be positioned within the housing 130. The getters 155 aid in creating and maintaining a vacuum condition of high quality. The getter has an activation temperature, after which it will react with stray gas molecules in the vacuum. It is desirable that the getter used have an activation temperature that is not so high that the x-ray device will be damaged when heated to the activation temperature.

The fiber optic cable 113 is adapted to transmit laser radiation, generated by the laser source 104 (shown in FIG. 3) and incident on the proximal end 113A of the fiber optic cable 113, to the distal end 113B of the fiber optic cable 113. The fiber optic cable 113 is also adapted to deliver a beam of the transmitted laser radiation to impinge upon the electron-emissive surface of the thermionic cathode 122. The beam of laser radiation must have a power level sufficient to heat at least a portion of the electron-emissive surface to an electron emitting temperature so as to cause thermionic emission of electrons from the surface.

In operation, the laser beam shining down the fiber optic cable 113 impinges upon the surface of the thermionic cathode 122, and rapidly heats the surface to an electron emitting temperature, below the melting point of the metallic cathode 122. Upon reaching of the surface of a electron emitting temperature, electrons are thermionically emitted from the surface. The high voltage field between the cathode 122 and the target element 128 (shown in FIGS. 3 and 4) accelerates these electrons, thereby forcing them to strike the surface of the target element 128 and produce x-rays. In one embodiment of the invention, a Nd:YAG laser was coupled into a SiO2 optical fiber having a diameter of 400 microns. A 20 kV power supply was used, and a thermionic cathode made of tungsten was used. Only a few watts of power was needed to generate over 100 $\mu$A of electron current. In another example, an infrared diode laser was used to achieve about 100 $\mu$A of electron current with only 180 mW of power.

Figure 6:
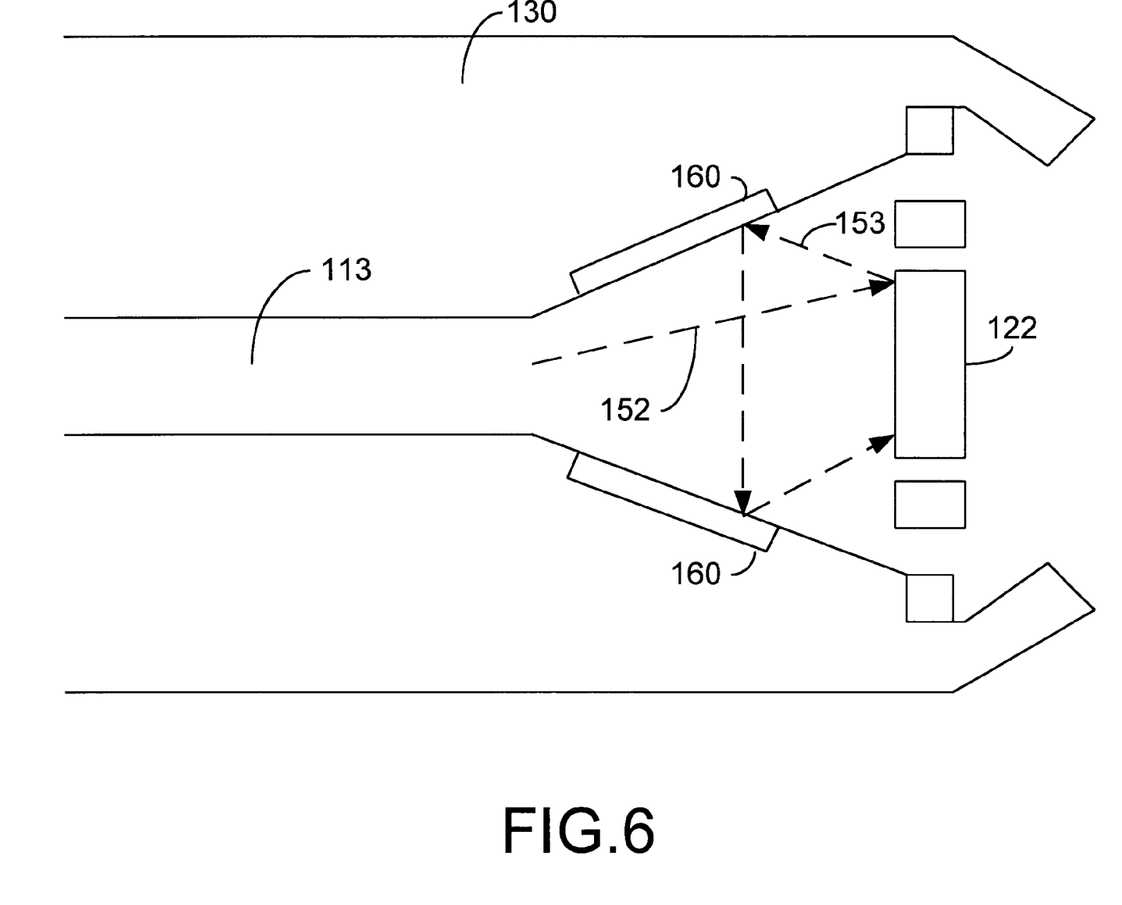
FIG. 6 is an enlarged view of one embodiment of an electron source embodying the present invention, illustrating reflector elements which reflect back to the laser-heated thermionic cathode laser radiation that was unabsorbed by the thermionic cathode.

Another way to increase the efficiency of the laser heated thermionic cathode, besides using laser energy to drive the thermionic cathode, is to minimize heat loss due to incident laser radiation that remains unabsorbed by the thermionic cathode. FIG. 6 illustrates one embodiment of an electron source embodying the present invention, in which reflector elements 160 are included which reflect back to the thermionic cathode 122 incident laser radiation that was unabsorbed by the thermionic cathode 122. FIG. 6 shows an illustrative incident ray 152 of laser radiation which is unabsorbed and scattered by the thermionic cathode 122. The scattered ray 153 of laser radiation impinges upon the inner surface of the capsule 130 enclosing the radiation generator assembly 101. By placing reflector elements 160 at predetermined locations along the inner surface of the capsule 130, incident laser radiation that remained unabsorbed by the electron emissive surface of the thermionic cathode 122 is reflected back by the reflector elements 160 to the thermionic cathode 122, so that an optical cavity is effectively created within the capsule. The coupling efficiency of the incident laser radiation to the thermionic cathode 122 is thereby significantly increased.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A therapeutic radiation source, comprising:
   A. a probe assembly including an optical delivery structure having a proximal end and a distal end, said optical delivery structure being adapted for transmitting optical radiation incident on said proximal end to said distal end;
   B. an optical source, including means for generating a beam of optical radiation directed to said proximal end of said optical delivery structure;
   C. a radiation generator assembly coupled to said probe assembly, including:
      a. an electron source, responsive to optical radiation transmitted to said distal end of said optical delivery structure, for emitting electrons, the electron source including a thermionic cathode having an electron emissive surface; and
      b. a target element including at least one radiation emissive material adapted to emit therapeutic radiation in response to incident accelerated electrons from said electron source; and
   D. means for providing an accelerating voltage between said electron source and said target element so as to establish an accelerating electric field which acts to accelerate electrons emitted from said electron source toward said target element;
   wherein said optical delivery structure is adapted for directing a beam of optical radiation transmitted therethrough to impinge upon a surface of said thermionic cathode, and wherein said beam of transmitted optical radiation has a power level sufficient to heat at least a portion of said surface to an electron emitting temperature so as to cause thermionic emission of electrons from said surface.

2. A therapeutic radiation source according to claim 1, wherein said optical source is a laser, and wherein said beam of optical radiation is substantially monochromatic and coherent.

3. A therapeutic radiation source according to claim 1, wherein said electron emissive surface of said thermionic cathode is formed of a metallic material.

4. A therapeutic radiation source according to claim 3, wherein said metallic material includes tungsten, thoriated tungsten, tungsten alloys, thoriated rhenium, and tantalum.

5. A therapeutic radiation source according to claim 1, wherein the emitted electrons form an electron beam along a beam path, and wherein said target assembly is positioned in said beam path.

6. A therapeutic radiation source according to claim 1, wherein said electron beam is characterized by a current in the approximate range of about 1 nA to about 1 mA.

7. A therapeutic radiation source according to claim 6, further including selectively operable control means for selectively controlling the amplitude of said beam current.

8. A therapeutic radiation source according to claim 1, wherein said electrons incident on said target element from said electron emissive surface are accelerated by said accelerating electric field to energies in the approximate range of 10 keV to 90 keV.

9. A therapeutic radiation source according to claim 1, wherein the means for providing an accelerating voltage includes:
a power supply, having a first terminal and a second terminal, and a drive means for establishing an output voltage between said first terminal and said second terminal, said power supply being electrically coupled to said radiation generator assembly by way of said first terminal and said second terminal.

10. A therapeutic radiation source according to claim 9, wherein said first terminal of said power supply is electrically coupled to said electron emissive surface of said thermionic cathode and said second terminal of said power supply is electrically coupled to said target element, thereby establishing an electric field which acts to accelerate electrons emitted from said electron emissive surface of said thermionic cathode toward said target element.

11. A therapeutic radiation source according to claim 9, wherein said second terminal is at ground potential.

12. A therapeutic radiation source according to claim 9, wherein said power supply further includes selectively operable control means for selectively controlling the amplitude of said output voltage.

13. A therapeutic radiation source according to claim 1, wherein said thermionic cathode includes a metallic base coated with an oxide.

14. A therapeutic radiation source according to claim 13, wherein said oxide includes barium oxide, strontium oxide, and calcium oxide, and said metallic base includes nickel.

15. A therapeutic radiation source according to claim 1, wherein said optical delivery structure includes a fiber optic cable.

16. A therapeutic radiation source according to claim 15, wherein said probe assembly includes a flexible, electrically conductive catheter enclosing said fiber optic cable.

17. A therapeutic radiation source according to claim 16, wherein said electrically conductive catheter is adapted for coupling said second terminal of said power supply to said radiation generator assembly.

18. A therapeutic radiation source according to claim 16, wherein the means for establishing an accelerating voltage includes a power supply, said power supply having a first terminal and a second terminal, said power supply being electrically coupled to said radiation generator assembly by way of said first terminal and said second terminal.

19. A therapeutic radiation source according to claim 18, wherein said fiber optic cable includes an electrically conductive outer surface, said electrically conductive outer surface being adapted for electrically coupling said first terminal of said power supply to said thermionic cathode.

20. A therapeutic radiation source according to claim 19, further comprising a layer of dielectric material between said electrically conductive outer surface of said fiber optical cable and an inner surface of said flexible catheter.

21. A therapeutic radiation source according to claim 1, further including:
a substantially rigid capsule, wherein said electron source and said target element are disposed within said capsule, and further wherein said capsule defines a substantially evacuated interior region extending along a beam axis between said thermionic cathode at a proximal end of said capsule and said target element at a distal end of said capsule.

22. A therapeutic radiation source according to claim 1 wherein said therapeutic radiation includes x-rays.

23. A therapeutic radiation source according to claim 1, wherein power required to heat said electron emissive surface of said cathode so as to generate an electron beam forming a current of about 100 micro amps is between about 0.1 Watts to about 3.0 Watts.

24. A therapeutic radiation source according to claim 1, wherein said target element is spaced apart and opposite said electron emissive surface of said thermionic cathode.

25. A source of therapeutic radiation, comprising:

A. a radiation generator assembly, including:
a. an electron source for emitting electrons to generate an electron beam along a beam path, wherein said electron source includes a thermionic cathode having an electron emissive surface; and
b. a target element positioned in said beam path, said target element being spaced apart from and opposite said electron emissive surface, said target element comprising at least one radiation emissive element adapted to emit therapeutic radiation in response to incident accelerated electrons from said electron beam; and
c. a substantially rigid capsule, wherein said electron source and said target element are disposed within said capsule, and further wherein said capsule defines a substantially evacuated interior region extending along a beam axis between said thermionic cathode at a proximal end of said housing and a radiation transmissive window at a distal end of said housing;

B. a source of laser radiation;

C. a probe assembly coupled to said radiation generator assembly and including an optical delivery structure, said optical delivery structure having a proximal end and a distal end;

wherein said optical delivery structure is adapted for transmitting laser radiation, generated by said source and incident on said proximal end, to said distal end, and for directing a beam of said transmitted laser radiation to impinge upon said electron emissive surface of said thermionic cathode, and wherein said beam of laser radiation has a power level sufficient to heat at least a portion of said surface to an electron emitting temperature so as to cause thermionic emission of electrons from said surface;

D. one or more reflector elements disposed at predetermined locations along an inner surface of said capsule, said one or more reflector elements being operative to reflect incident laser radiation unabsorbed by said thermionic cathode back to said thermionic cathode.

* * * * *